(12) United States Patent
Watkins et al.

(10) Patent No.: US 11,164,683 B2
(45) Date of Patent: Nov. 2, 2021

(54) ELECTRON BLOCK FRAME POURING FIXTURE

(71) Applicants: Robert Watkins, Dandridge, TN (US); Karen Jackson, Dandridge, TN (US)

(72) Inventors: Robert Watkins, Dandridge, TN (US); Karen Jackson, Dandridge, TN (US)

(*) Notice: Subject to any disclaimer, the term of this patent is extended or adjusted under 35 U.S.C. 154(b) by 98 days.

(21) Appl. No.: 16/560,539

(22) Filed: Sep. 4, 2019

(65) Prior Publication Data

US 2020/0161012 A1    May 21, 2020

Related U.S. Application Data

(60) Provisional application No. 62/768,041, filed on Nov. 15, 2018.

(51) Int. Cl.

| | |
|---|---|
| *B22C 9/06* | (2006.01) |
| *B22D 33/00* | (2006.01) |
| *B28B 7/00* | (2006.01) |
| *B25B 5/14* | (2006.01) |
| *G21F 3/04* | (2006.01) |
| *A61B 6/10* | (2006.01) |
| *B25B 5/00* | (2006.01) |
| *A61N 5/10* | (2006.01) |

(52) U.S. Cl.
CPC ............. *G21F 3/04* (2013.01); *A61B 6/107* (2013.01); *B25B 5/14* (2013.01); *A61N 2005/1089* (2013.01); *A61N 2005/1094* (2013.01); *B25B 5/003* (2013.01)

(58) Field of Classification Search
CPC .......... B22C 9/06; B22D 33/00; B22D 33/04; B28B 7/00; B25B 5/003; B25B 5/006; B25B 5/12; B25B 5/14
USPC ........... 164/47, 271, 339, 341, 342; 249/117
See application file for complete search history.

(56) References Cited

U.S. PATENT DOCUMENTS 1,815,230 A * 7/1931 Boynton ................ B23Q 3/086
144/259

OTHER PUBLICATIONS

Karen Jackson and Robert Watkins, Inventor Obtained Photos of Conventional Device, prior to Nov. 15, 2018.
RP Design, Inc.,Varian Type III with Acrylic Drawing plate set, https://www.rpdinc.com/varian-type-III-with-mlc-acrylic-drawing-plate-set-4378.html, prior to Nov. 15, 2018.
RP Design, Inc.,Cooling Plate for Varian III Electron Cone Insert, https://www.rpdinc.com/cooling-piate-for-varian-iii-electron-cone-insert-frames-8715.html, prior to Nov. 15, 2018.
RP Design, Inc.,Varian III with MLC, https://www.rpdinc.com/varian-iii-with-mlc-insert-frame-for-electron-cone-block-20-x-20cm-refurbished-4386.html, prior to Nov. 15, 2018.

(Continued)

*Primary Examiner* — Kevin P Kerns
(74) *Attorney, Agent, or Firm* — Pitts & Lake, P.C.

(57) ABSTRACT

An electron block frame pouring fixture, and a method of using the fixture, the fixture including a base member having a recessed portion surrounded on each side, the recessed portion configured to receive an electron block frame therein, and a plurality of clamp members connected to the base member proximate each of the respective sides of the recessed portion, the clamp members being configured to be selectively actuated to press a received electron block frame downward into the recessed portion, wherein the recessed portion is configured to prevent lateral movement of the received electron block frame.

9 Claims, 5 Drawing Sheets

(56) References Cited

OTHER PUBLICATIONS

RS&A, Varian, https://www.oncologyparts.com/collections/varian/electron-cones?page=1, prior to Nov. 15, 2018.
Varian Medical Systems, Clinac iX Accelerator, 2014 Varian Medical Systems Inc.

* cited by examiner

ELECTRON BLOCK FRAME POURING FIXTURE

CROSS-REFERENCE TO RELATED APPLICATIONS

This application claims the benefit of U.S. Provisional Patent Application Ser. No. 62/768,041, filed on Nov. 15, 2018, which is incorporated herein in its entirety by reference.

FIELD OF INVENTION

The present general inventive concept relates to forming an electron block, and, more particularly, to a fixture used to hold an electron blocking frame when pouring an electron block.

BACKGROUND

Radiation therapy is used to treat many types of cancers, and an electron block is a commonly used product in radiation therapy. Electron radiotherapy is used to treat superficial areas and postoperative cancer sites. Due to the irregular shape of the typical treated area, custom blocking is needed to protect the surrounding healthy tissue from radiation exposure. Hence, the previously mentioned electron block is used to shield the healthy tissue from that exposure. The traditional process employed to form (by pouring) these electron blocks requires the use of acrylic trays, such as Lucite®, on which the physician draws the shape of the required block for the patient treatment. This acrylic tray is then used as a template, with which the drawn shape is transferred to Styrofoam®, and cut out of the Styrofoam® to create an opening in the treatment field specific to that patient. A molten alloy such as Cerrobend® is poured around the foam inside an electron block frame, which is clamped atop the acrylic tray during the forming of the electron block, that will hold the formed block and be used to insert the block into the electron cone on the linear accelerator. The process for each facility can vary, but typically involves the use of metal spring clamps on opposite sides of the electron block frame to hold the acrylic tray and electron block frame together. As the spring clamps extend below and above the plane of the frame, it is problematic to hold the frame level for block pouring and cooling. Given the geometry of the spring clamps, they could be attached to the frame and tray at an angle that would allow for the frame to be somewhat level on the surface on which it was being used, but there is an additional problem where the clamp grip edge will extend into the frame and poured block area causing indention/inconsistent thickness of the poured block, therefore decreasing the ability of the block to adequately protect the normal tissue from the radiation.

Additionally, most radiation clinics are using a newer, less toxic alloy, which requires a higher melting temperature but causes some deformation of the block frames due to high heat and pressure of the block material along the sides of the frames. Bulging frames will not fit into the linear accelerator applicator insert correctly, which could cause delay in patient treatment and even damage to the electron cone insert itself, which could be costly to repair.

Therefore, it would be desirable to be able to pour an electron block without at least the problems described above regarding the clamps and frame deformation, and one which would increase a level of convenience when pouring the electron block.

BRIEF SUMMARY

According to various example embodiments of the present general inventive concept, an electron block frame pouring fixture is provided that can prevent deformation of the frame during the pouring and forming of the electron block by supporting sides of the frame. Embodiments of the present general inventive concept may also provide clamping members to clamp the frame down without contacting the molten alloy.

Additional aspects and advantages of the present general inventive concept will be set forth in part in the description which follows, and, in part, will be obvious from the description, or may be learned by practice of the present general inventive concept.

The foregoing and/or other aspects and advantages of the present general inventive concept may be achieved by providing an electron block frame pouring fixture including a base member having a recessed portion surrounded on each side, the recessed portion configured to receive an electron block frame therein, and a plurality of clamp members connected to the base member proximate each of the respective sides of the recessed portion, the clamp members being configured to be selectively actuated to press a received electron block frame downward into the recessed portion, wherein the recessed portion is configured to prevent lateral movement of the received electron block frame.

The foregoing and/or other aspects and advantages of the present general inventive concept may also be achieved by providing a method of pouring an electron block, the method including providing a fixture having a recessed portion with a first section stepped down from a top surface of the fixture, and a second section stepped down from the first section and located centrally in the first section, placing a support tray in the second section such that lateral motion of the support tray is prevented, placing an electron block frame in the first section such that the electron block frame rests on top of the support tray and is prevented from lateral movement by the recessed portion of the fixture, clamping the electron block frame down so as to form a seal between the electron block frame and support tray, placing an electron block pattern on top of the support tray, and pouring a molten alloy over the support tray, to a desired depth, to form an electron block on portions of the support tray not covered by the electron block pattern.

Other features and aspects may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be simplified and/or omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

According to various example embodiments of the present general inventive concept, an electron block frame pouring fixture is provided that can prevent deformation of the electron block frame during the pouring and forming of the electron block by supporting sides of the frame so as to prevent lateral bulging or overall lateral movement of the frame. Embodiments of the present general inventive concept may also provide clamping members to clamp the frame down without contacting the molten alloy. Various example embodiments of the present general inventive concept provide a fixture having a "pocket," recess, receiving portion, etc., in which the electron block frame may be placed such that the frame is supported at each side, and also clamped down from above by a plurality of the clamping members that press down upon the frame when employed. The fixture may also have a deeper recess, stepped down from the first recess which surrounds the electron block frame to prevent lateral movement, that holds a support tray which is also supported from underneath and at all sides to prevent lateral movement. The electron block frame may then be positioned above the support tray and pressed, or biased, down onto the support tray tightly enough to provide a seal therebetween through which molten alloy material cannot pass. Thus, the molten alloy can then be poured into the electron block frame, contacting the top of the support tray and the inner sides of the electron block frame, and forming around the block pattern which is also rested on the support tray. After cooling, the electron block frame, which now holds the electron block in its predetermined configuration, may be easily removed from the fixture.

Figure 1:
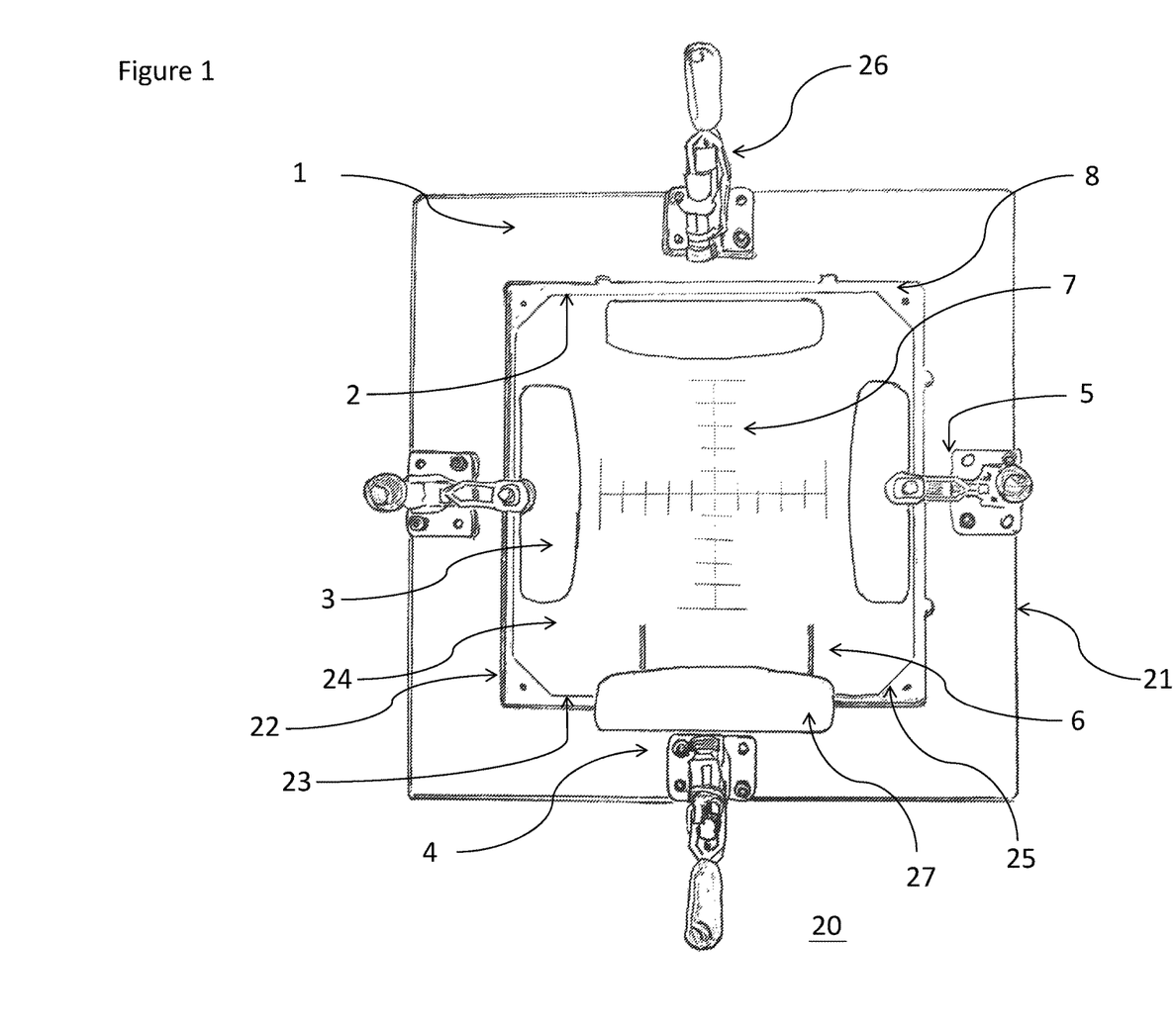
FIG. 1 illustrates a top view of an electron block frame pouring fixture according to an example embodiment of the present general inventive concept.

FIG. 1 illustrates a top view of an electron block frame pouring fixture according to an example embodiment of the present general inventive concept. According to various example embodiments, portions or all of the electron block frame pouring fixture 20 may be milled out of a single piece of aluminum. As illustrated, a base member 21 of the frame may have a baseplate 1 bordering a recessed portion 22 configured with a first section 23 stepped down from the baseplate 1 and formed to hold an electron block frame, and a second section 24 stepped down from the first section 23 and formed to hold a support tray, such as a Lucite® tray. As illustrated in FIG. 1, the first section 23 is formed by vertical walls 8 stepped down from the baseplate 1, and the second section 24 is formed by vertical walls 2 stepped down from the first section 23. Thus, the first section 23 is formed as a ridge extending about the boundary of the recessed portion 22, and thus supports the electron block frame when such a frame is placed in the fixture 20, but is open in most of the center thereof so that molten alloy may be poured on a support tray placed in the lower second section 24. As illustrated in FIG. 1, the step forming the second section 24 may be substantially square, and chamfered corners 25 may be formed by the first section 23 to correspond to the corners of the electron block frame.

As illustrated in FIG. 1, the fixture 20 may have one or more access cutouts or openings 3 to allow a user to access a bottom surface of a support tray received in the second section 24. In various example embodiments a plurality of the openings 3 may be provided proximate each side of the second section 24. Such a feature may aid in popping the support tray and formed electron block out of the fixture 20 after cooling of the alloy forming the block. Various example embodiments may include a cutout 27 that extends further outward from the rest of the border of the recessed portion 22 so as to receive a code reader tab portion provided on the electron block frame. Additionally, various example embodiments of the present general inventive concept may provide milled alignment marks 6 on the floor of the second section 24 that correspond with alignment notches provided on the support tray, to give quick and easy guidance on the proper alignment of the support tray. The second section 24 may also include engraved grid lines 7 to aid in placing the block form on top of the support tray before pouring the molten alloy.

As illustrated in FIG. 1, the fixture 20 includes a plurality of clamping members 26 attached on to the base member 21 proximate each side of the recessed portion 22. The clamping members 26 are configured to contact and press an electron block frame tightly against the support tray when actuated, so as to provide a seal such that molten alloy does not leak between the electron block frame and support tray during forming of the electron block. Referring to FIG. 1, identifier 4 indicates a clamping member in an "open" position, and identifier 5 indicates a clamping member 26 in a "closed" position. The clamping members 26 will be discussed in more detail herein.

Figure 2:
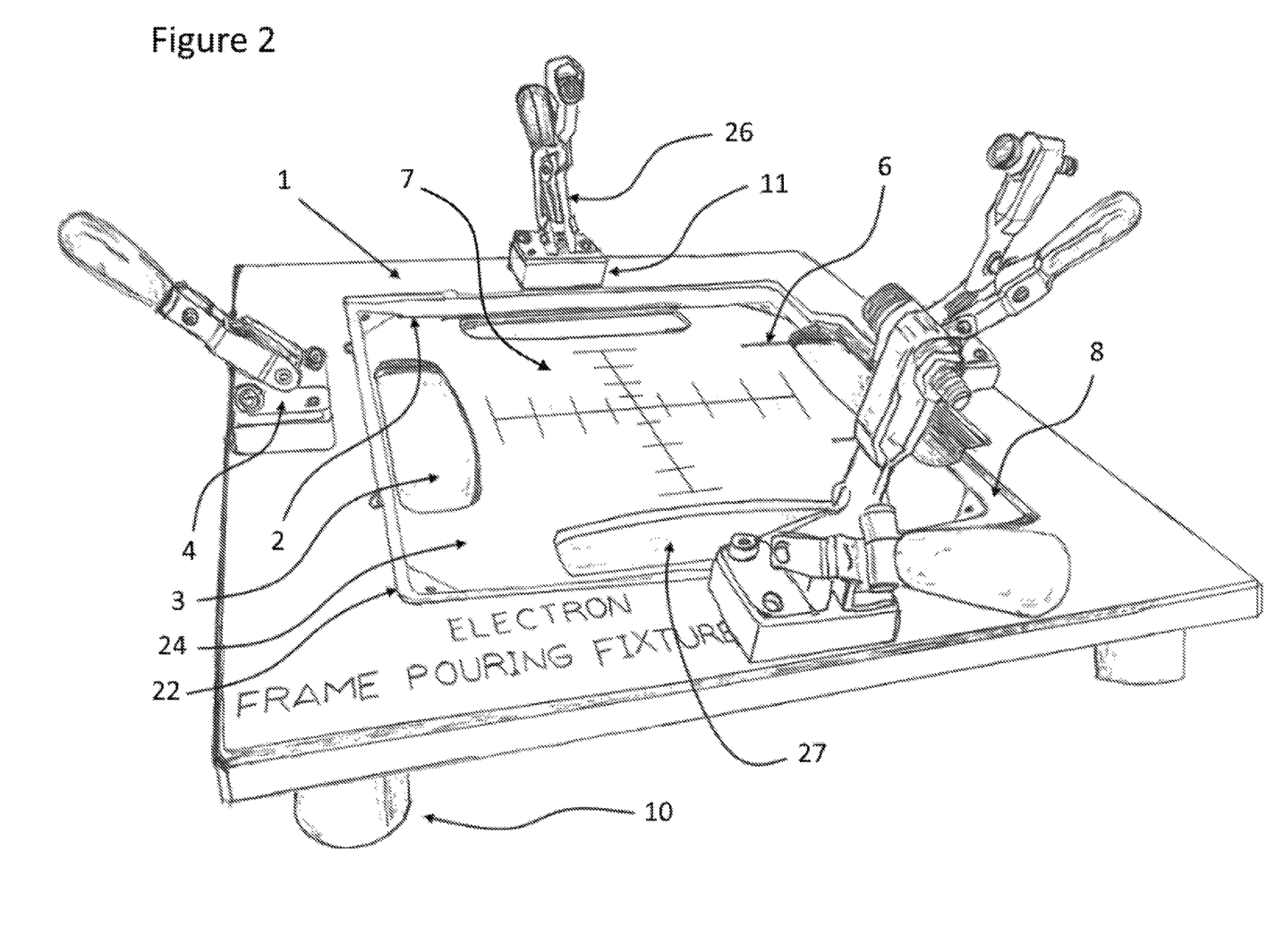
FIG. 2 illustrates a perspective view of the electron block frame pouring fixture of FIG. 1.

FIG. 2 illustrates a perspective view of the electron block frame pouring fixture of FIG. 1. As illustrated in FIG. 2, the fixture 20 may include a plurality of feet 10 to raise the rest of the fixture 20 off of the surface on which it sits, which can aid in the cooling of the alloy when forming the electron block. In various example embodiments the feet 10 may be cylindrical aluminum feet. As illustrated in FIG. 2, riser blocks 11 may be provided to elevate the clamps 26 to a position to aid in securely holding the electron block frame against the support tray.

Figure 3:
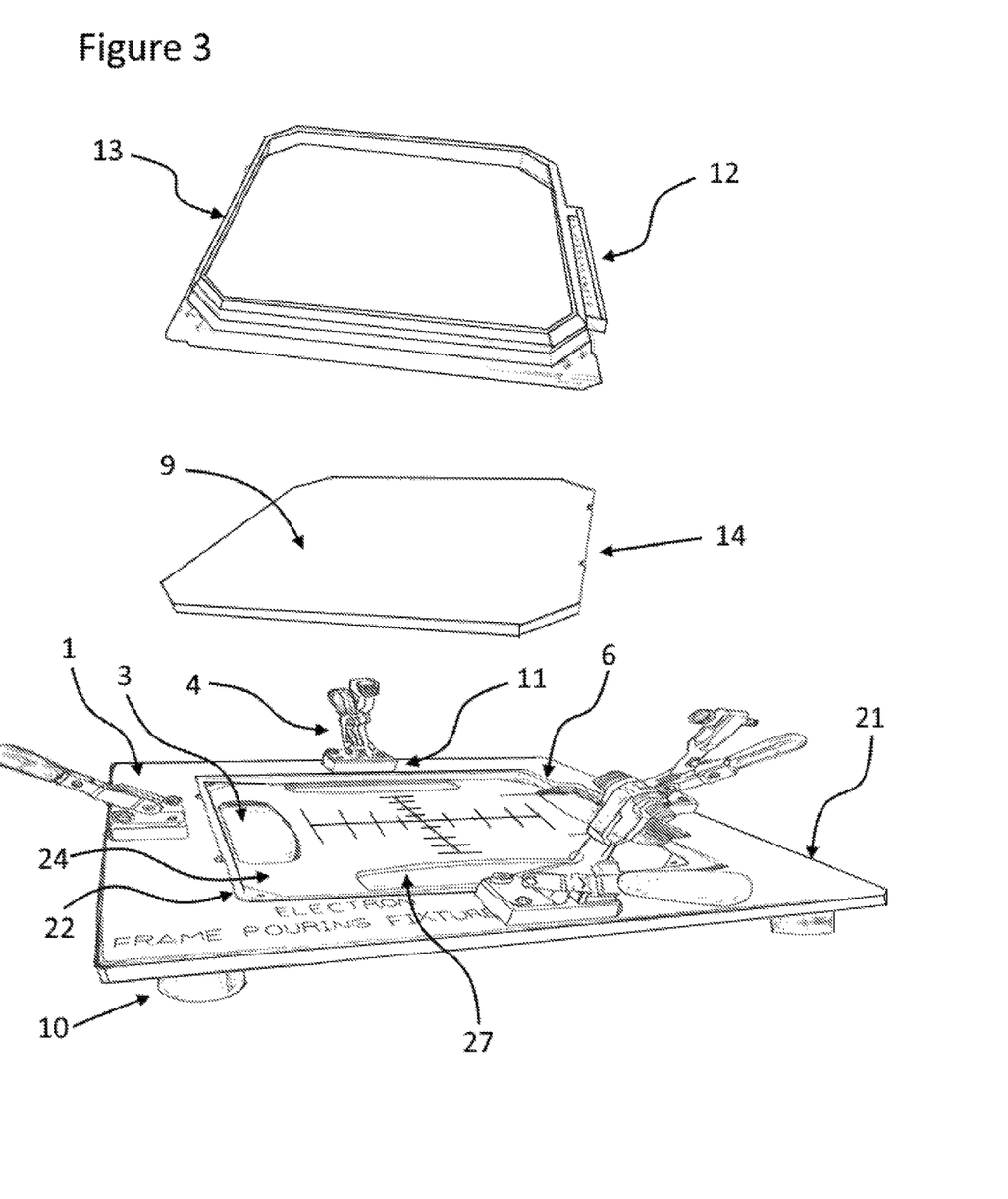
FIG. 3 illustrates the electron block frame pouring fixture of FIG. 1 along with components used to pour an electron block according to an example embodiment of the present general inventive concept.

FIG. 3 illustrates the electron block frame pouring fixture of FIG. 1 along with components used to pour an electron block according to an example embodiment of the present general inventive concept. As illustrated in FIG. 3, the support tray 9 is formed in a shape that corresponds to the second section 24 of the recessed portion 22, and include tray alignment notches 14 that correspond with the alignment marks 6 formed on the floor of the second section 24 to guide a user in the placement of the support tray 9. An electron block frame 13 is shown as having a labeled code reader tab 12.

Figure 4:
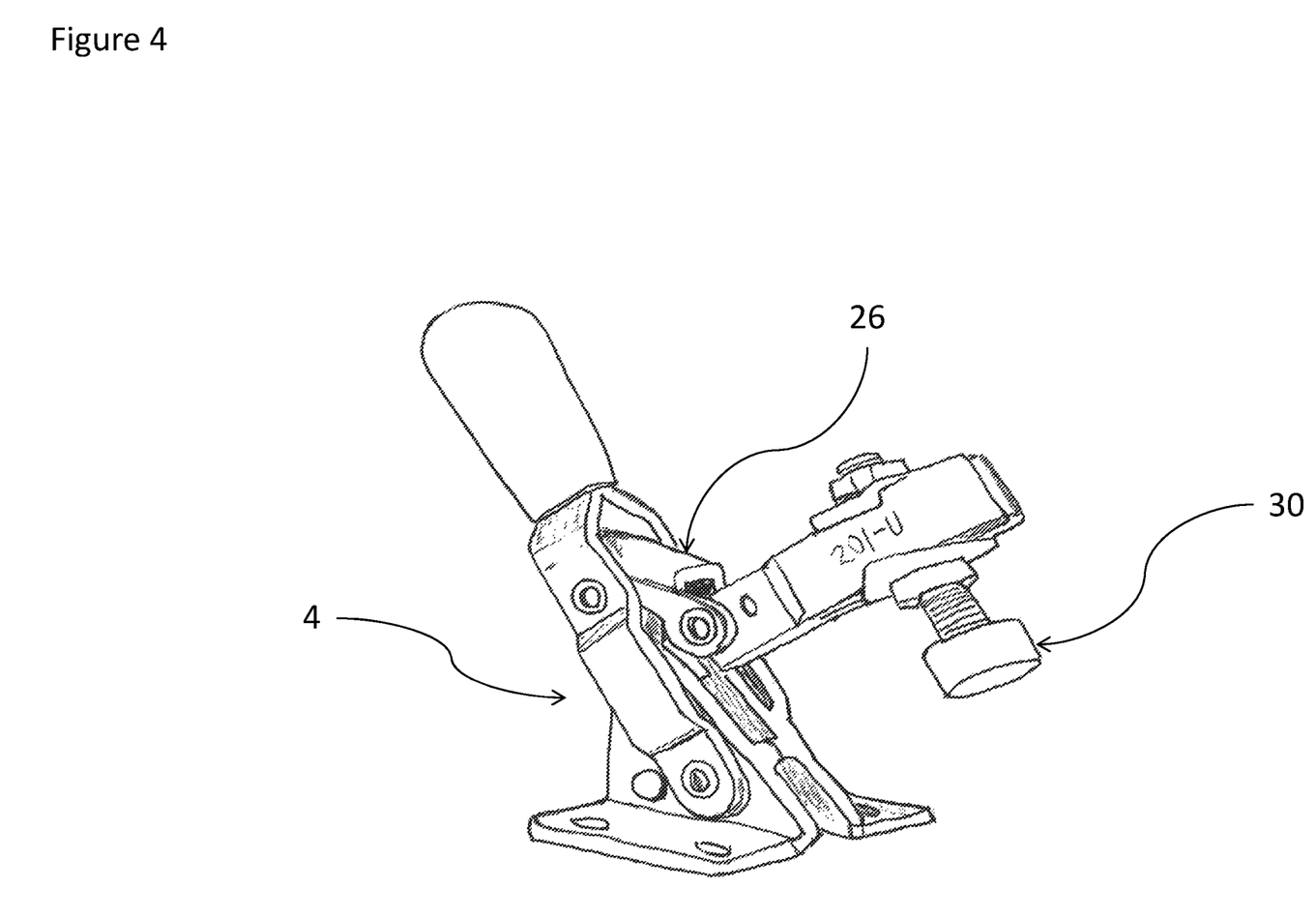
FIG. 4 illustrates a clamping member used in an electron block frame pouring fixture according to an example embodiment of the present general inventive concept.

FIG. 4 illustrates the clamping member 26 used in an electron block frame pouring fixture according to an example embodiment of the present general inventive concept. The clamping member 26 is illustrated in FIG. 4 in the "open" position 4. The clamping member 26 is provided with a contact portion 30 that is configured to contact an upper edge of the electron block frame 13 when the frame 13 is received in the first section 23 of the recessed portion 22 of the fixture 20. When the clamping member 26 is manipulated to the "closed" position, the contact portion 30 contacts the electron block frame 13 to press the frame 13 down onto the support tray 9 with sufficient force to prevent molten alloy from seeping between the two when the alloy is poured over the support tray 9. Also, since none of the contact portion 30 or any other part of the clamping member 26 protrudes downward from an upper edge of the frame 13 in an area inside the frame 13, the clamping member 26 does not interfere in any way with any alloy poured inside the frame 13. Also, in various example embodiments the clamping members 26 are located such that the contact with the frame 13 is proximate a mid-point of that respective side of the frame 13, to enhance the distribution of force provided by the clamping members 26 onto the frame 13. It is noted that a host of different clamping members may be employed to provide the pressure to the frame 13 without departing from the scope of the present general inventive concept. Many such clamping members similar to that illustrated in FIG. 4 are available commercially for implementation or replacement.

Figure 5:
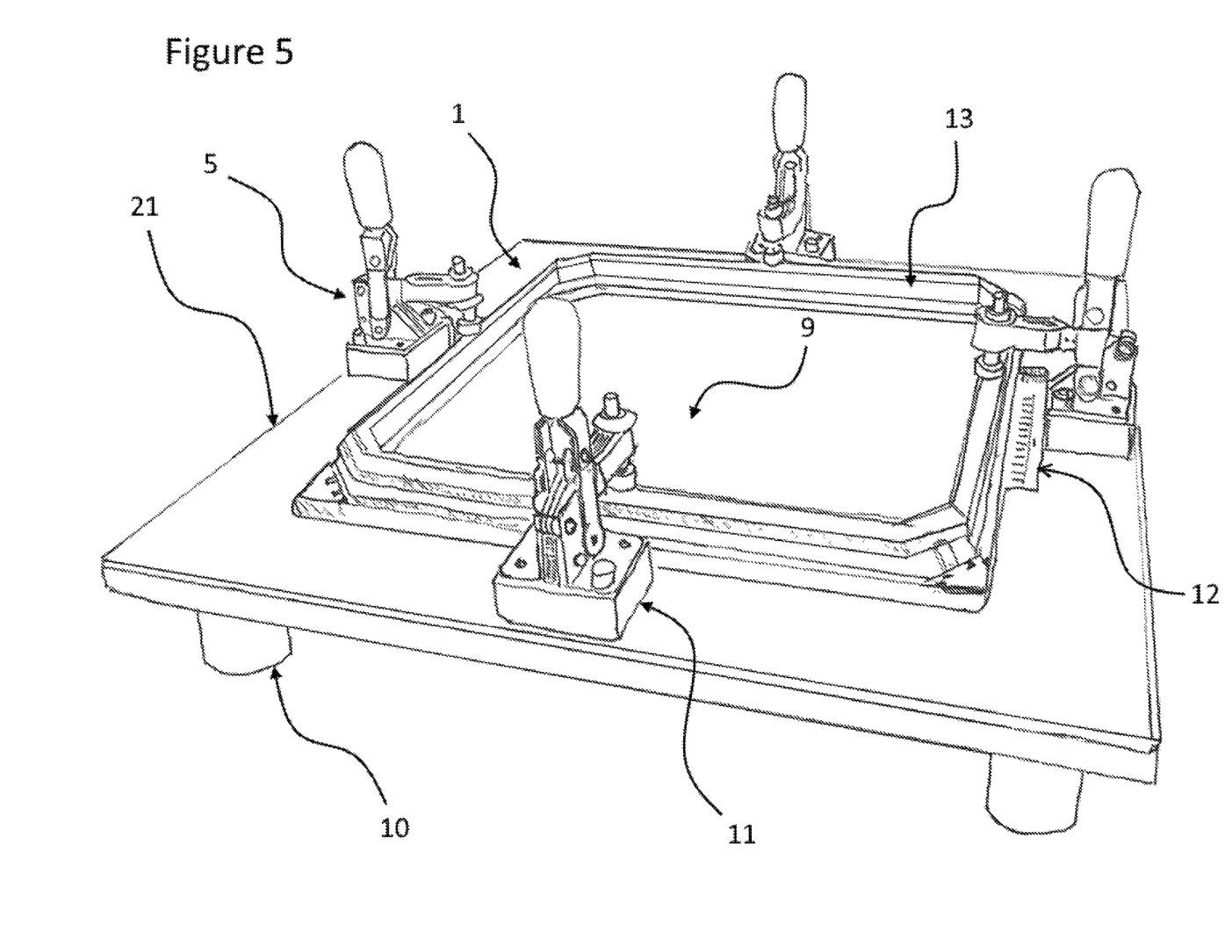
FIG. 5 illustrates the articles of FIG. 3 assembled together to pour an electron block according to an example embodiment of the present general inventive concept.

FIG. 5 illustrates the articles of FIG. 3 assembled together to pour an electron block according to an example embodiment of the present general inventive concept. In FIG. 5, the support tray 9 has been placed in the second section 24 such that it is supported from underneath and on all sides. The openings 3 and the portion of the cutout 27 located underneath the support tray 9 have been omitted from the drawing for the sake of clarity. After the placement of the support tray 9, the electron block frame 13 has been placed over the support tray and in the first section 23 so that it is supported on all sides by the walls of the first section 23. The clamps 26 have been "closed" to fix the electron block frame 13 in place to provide a sealed contact with the support tray 9. As illustrated in FIG. 5, the code reader tab 12 is received in the cutout 27. The fixture 20 and assembled support tray 9 and electron block frame 13 are now in a state that is ready for a block pattern to be placed on the support tray 9, at which point the molten alloy may be poured onto the support tray 9 to form the electron block. After the alloy has cooled, the clamps 26 may be opened, and a user can press up through the openings 3 to push the support tray 9, and therefore, the formed electron block and electron block frame 12, out of the fixture 20.

The concept of the electron block frame pouring fixture was born from the issues radiation therapy clinics experience with the frames that contain the radiation blocking material, Cerrobend®, bulging out of square due to heat and pressure of the block material. The deformation, or bulging, of the frame causes the frame to not seat properly in the linear accelerator's mounting accessory, which disables the ability to deliver the planned therapeutic radiation dose to the patient. In addition, if or when, force is used to push a bulged electron block frame into the mounting accessory, frequently damage is done to the accessory, including damage to the code reader which functions to ensure that the designated block for a specific patient is being used in that treatment. Damage to the accessory mount or code reading device is costly to repair and can cause problems with treating all other patients whose treatment requires that particular accessory until repairs can be made, delaying treatment by hours or possibly days. Although the bulging frames can create issues with any accelerator, it can be especially problematic for the new high precision linear accelerators, which have tighter tolerances for accessories. Not only can the repairs be costly, but delayed patient treatments could reduce the therapeutic outcome of the patient's radiation course, waste time of the patient and staff, and give the patient an overall poor experience and lack of confidence in their treatment. Some facilities are disposing of the damaged frames, and are having to re-make the required blocks for the patients in a new, costly frame, occasionally more than twice. Some sites try pouring with product that has been allowed to cool, to reduce heat warping, causing inconsistencies in the blocking material itself, or pour a thinner layer of the material, to reduce the pressure on the frame. Both of these strategies could result in insufficient blocking of the radiation to the patient's healthy tissue. Even if the clinic is not having issues with bulged electron block frames not seating in the accessory, most facilities are using a piecemeal method of clamping the Lucite® tray, which details the physician's prescribed blocking shape, to the frame and trying to come up with a way to levelly balance the clamped frame on a system of bars to get a useful poured block. Many times the clamps prohibit the frame from being level and also protrude into the block material causing thin spots and inconsistencies in the radiation block material, thus reducing its effectiveness in protecting the patient's healthy tissue.

The electron block frame pouring fixture according to the present general inventive concept addresses these issues with electron block pouring. The fixture may be machined to exact dimensions out of a solid piece of aluminum stock with a pocket to contain the Lucite® tray with the delineated block shape, and the edges of the frame itself that will not allow any bulging out of square, even under heat and pressure. The fixture will ensure that the frame will fit into the accessory mount without force or damage. Additionally, the fixture has an easy to use clamping system that will hold the Lucite® tray and frame, level and secure, allowing the user to achieve a precision, uniform block to better protect the patient's healthy tissue. The fixture material has an additional benefit of being a heat sink, allowing the poured block to cool more rapidly. This increased cooling rate can speed the production of the required patient radiation blocks. Additionally, the product can correct the bulging in previously, slightly damaged electron block frames, thus reducing expenses involved in replacing damaged frames. Ensuring that the radiation blocking device will fit into the accessory mount, function properly with the code reader, block the radiation to healthy tissue where prescribed, and will allow the patient to receive their treatments in an effective and timely manner is the ultimate goal of all radiation therapy clinics.

Various example embodiments of the present general inventive concept may provide an electron block frame pouring fixtures including a square aluminum base plate having a recessed pocket to align a support tray and electron block frame in the correct location and orientation. The recessed pocket may include one pocket to hold the support tray, and a larger, more shallow, machined pocket to contain the electron block frame and prevent bulging or deformation of the electron block frame during pouring and cooling of the pouring material. The fixture may include offset clamps to apply pressure to the frame and tray against the base plate to prevent leakage of the poured block material in the frame. The base plate may have cutout/relief areas to allow for finger pressure to be applied upward from below to remove the block, tray, and frame from the fixture once block has cooled. The fixture may be equipped with four jig feet, one being provided in each corner, to hold the fixture level and suspended off of the surface on which it is being used, which promotes faster cooling of the block material and access to the cutouts to apply the upward pressure to the frame and tray.

In various example embodiments of the present general inventive concept, the electron block frame pouring fixture may be machined to exact dimensions out of a solid piece of aluminum stock, with a pocket to contain the support tray (such as Lucite®) with the delineated block shape. The pocket may also have machined site marks for visually locating tabs on the support trays to ensure that the tray is in the correct orientation and location with respect to the electron block frame. The walls of the frame pocket may be configured to align and secure the edges of the frame itself, and to prevent any bulging out of square of the frame, even under heat and pressure. Once the alloy has cooled, the through holes in the bottom of the base plate allow for easy removal of the tray, frame, and block.

Various example embodiments of the present general inventive concept may provide an electron block frame pouring fixture including a base member having a recessed portion surrounded on each side, the recessed portion configured to receive an electron block frame therein, and a plurality of clamp members connected to the base member proximate each of the respective sides of the recessed portion, the clamp members being configured to be selectively actuated to press a received electron block frame downward into the recessed portion, wherein the recessed portion is configured to prevent lateral movement of the received electron block frame by providing substantially full perimeter support. The recessed portion may include a first section stepped down from an upper surface of the base member, and a second section stepped down from the first section, wherein the first section is configured to support the received electron block frame, and the second section is configured to receive a support tray to support poured block material. The clamping members may be configured to press the received electron block frame onto a received support tray to prevent the poured block material from passing in between. The second section may be configured to prevent lateral movement of a received support tray. The second section may have at least one opening at a bottom thereof to provide access to a received support tray from a bottom of the base member. The second section may have at least one opening at a bottom thereof that extends outward from one of the sides of the first section, and is configured to receive a code reader tab of the received electron block frame. The clamping members may be respectively located proximate mid points of each side of the recessed portion. The clamping members may be configured so as not to extend lower than a top edge of a received electron block frame, in an area inside the received electron block frame, when actuated. The electron block frame pouring fixture may further include a plurality of feet extending downward from a bottom surface of the base member to provide a gap between the base member and a surface on which the electron block frame pouring fixture is placed. One or more alignment marks may be provided on a floor of the second section to correspond with support tray alignment marks. The one or more alignment marks may be milled. Grid lines may be formed on a floor of the second section to provide at least a partial grid that is visible through the support tray.

Various example embodiments of the present general inventive concept may provide a method of pouring an electron block, the method including providing a fixture having a recessed portion with a first section stepped down from a top surface of the fixture, and a second section stepped down from the first section and located centrally in the first section, placing a support tray in the second section such that lateral motion of the support tray is prevented, placing an electron block frame in the first section such that the electron block frame rests on top of the support tray and is prevented from lateral movement by the recessed portion of the fixture, clamping the electron block frame down so as to form a seal between the electron block frame and support tray, placing an electron block pattern on top of the support tray, and pouring a molten alloy over the support tray, to a desired depth, to form an electron block on portions of the support tray not covered by the electron block pattern. The clamping of the electron block frame may be performed by clamping members that are connected to the fixture and are selectively actuated to clamp the electron block frame. The method may further include aligning the support tray according to alignment marks formed on a floor of the second section. The method may further include arranging the electron block pattern over grid lines formed on a floor of the second section. The method may further include removing the formed electron block and electron block frame by pushing upward through at least one access opening formed in a floor of the second section. The method may further include placing a code reader tab of the electron block frame in a corresponding receiving portion of the fixture during the placing of the electron block frame in the first section.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. An electron block frame pouring fixture, comprising:
   a base member having a recessed portion surrounded on each side by an upper surface of the base member, the recessed portion comprising:
      a first section defined by first vertical walls extending down from the upper surface of the base member, and configured to support a removable electron block frame from underneath and to align and secure edges of each side of the electron block frame to prevent lateral movement,
      a second section defined by second vertical walls extending down from a lower surface of the first section, and configured to support a removable support tray from underneath and to align and secure edges of each side of the support tray to prevent lateral movement, the support tray configured to support poured block material, and
      at least one opening formed in a bottom surface of the base member so as to extend through to a bottom of the second section to provide access to a bottom surface of a received support tray through the bottom surface of the base member; and
   a plurality of clamp members connected to the base member proximate each of the respective sides of the recessed portion, the clamp members being configured to be selectively actuated to press a received electron block frame downward into the recessed portion.

2. The electron block frame pouring fixture of claim 1, wherein the clamping members are configured to press the received electron block frame onto the received support tray to prevent the poured block material from passing in between.

3. The electron block frame pouring fixture of claim 1, wherein the second section has at least one opening at a bottom thereof that extends outward from one of the sides of the first section, and is configured to receive a code reader tab of the received electron block frame.

4. The electron block frame pouring fixture of claim 1, wherein the clamping members are respectively located proximate mid points of each side of the recessed portion.

5. The electron block frame pouring fixture of claim 1, wherein the clamping members are configured so as not to extend lower than a top edge of a received electron block frame, in an area inside the received electron block frame, when actuated.

6. The electron block frame pouring fixture of claim 1, further comprising a plurality of feet extending downward from the bottom surface of the base member to provide a gap between the base member and a surface on which the electron block frame pouring fixture is placed.

7. The electron block frame pouring fixture of claim 1, wherein one or more alignment marks are provided on a floor of the second section to correspond with support tray alignment marks.

8. The electron block frame pouring fixture of claim 7, wherein the one or more alignment marks are milled.

9. The electron block frame pouring fixture of claim 1, wherein grid lines are formed on a floor of the second section to provide at least a partial grid that is visible through the support tray.

* * * * *